(12) United States Patent
Messana et al.

(10) Patent No.: US 9,994,510 B2
(45) Date of Patent: Jun. 12, 2018

(54) ANAEROBIC CURABLE COMPOSITIONS CONTAINING BLOCKED (METH)ACRYLIC ACID COMPOUNDS

(71) Applicant: Henkel IP & Holding GmbH, Duesseldorf (DE)

(72) Inventors: Andrew D. Messana, Newington, CT (US); Sean M. Burdzy, Hamden, CT (US); Joel D. Schall, Hamden, CT (US); Anthony F. Jacobine, North Haverhill, NH (US)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days. days.

(21) Appl. No.: 15/340,385

(22) Filed: Nov. 1, 2016

(65) Prior Publication Data

US 2017/0044088 A1 Feb. 16, 2017

Related U.S. Application Data

(63) Continuation of application No. PCT/US2015/028908, filed on May 1, 2015.

(60) Provisional application No. 62/061,389, filed on Oct. 8, 2014, provisional application No. 61/987,201, filed on May 1, 2014.

(51) Int. Cl.

| | |
|---|---|
| *C08F 20/06* | (2006.01) |
| *C08F 118/02* | (2006.01) |
| *C07C 69/60* | (2006.01) |
| *C08F 2/44* | (2006.01) |
| *C08F 220/28* | (2006.01) |
| *C09J 133/06* | (2006.01) |
| *C08L 33/06* | (2006.01) |
| *C09J 133/14* | (2006.01) |
| *C07C 69/54* | (2006.01) |
| *C09J 4/06* | (2006.01) |
| *C09K 3/10* | (2006.01) |
| *C08F 222/02* | (2006.01) |

(52) U.S. Cl.
CPC .............. *C07C 69/60* (2013.01); *C07C 69/54* (2013.01); *C08F 2/44* (2013.01); *C08F 220/28* (2013.01); *C08L 33/06* (2013.01); *C09J 4/06* (2013.01); *C09J 133/06* (2013.01); *C09J 133/14* (2013.01); *C08F 222/02* (2013.01); *C08F 2220/281* (2013.01); *C08F 2220/286* (2013.01); *C09K 2003/1065* (2013.01)

(58) Field of Classification Search
CPC .... C08F 2/44; C08F 220/28; C08F 2220/281; C08F 2220/286; C08F 222/06; C09J 133/06; C09J 133/14; C08L 33/06; C07C 69/60; C07C 69/54
USPC .............................................. 526/317.1, 319
See application file for complete search history.

(56) References Cited

U.S. PATENT DOCUMENTS

| | | | |
|---|---|---|---|
| 3,970,505 A | 7/1976 | Hauser et al. | |
| 4,215,209 A * | 7/1980 | Ray-Chaudhuri | C09J 4/00 523/176 |
| 4,287,350 A | 9/1981 | Huellstrung et al. | |
| 4,321,349 A | 3/1982 | Rich | |
| 4,324,349 A | 4/1982 | Kaufman | |
| 4,525,232 A | 6/1985 | Rooney et al. | |
| 5,411,988 A | 5/1995 | Bockow et al. | |
| 5,605,999 A | 2/1997 | Chu | |
| 6,048,587 A | 4/2000 | Estrin | |
| 7,728,092 B1 | 6/2010 | Jacobine et al. | |
| 7,951,884 B1 | 5/2011 | Birkett et al. | |
| 2005/0101689 A1* | 5/2005 | Woods | C08F 20/28 522/178 |
| 2009/0281335 A1 | 11/2009 | Messana et al. | |
| 2012/0168219 A1 | 7/2012 | Kitamura et al. | |
| 2014/0004353 A1 | 1/2014 | Birkett et al. | |

FOREIGN PATENT DOCUMENTS

| | | |
|---|---|---|
| WO | 9901484 | 1/1999 |
| WO | 2009014688 | 1/2009 |
| WO | 2011047123 | 4/2011 |
| WO | 2014043720 | 3/2014 |

OTHER PUBLICATIONS

International Search Report issued in connection with International Patent Application No. PCT/US2015/028908 dated Aug. 27, 2015.
R.D. Rich, "Anaerobic Adhesives" in Handbook of Adhesive Technology, 29, 467-79, A. Pizzi and K.L. Mittal, eds., Marcel Dekker, Inc., New York (1994).
International Search Report issued in connection with International Patent Application No. PCT/US2015/028829 dated Jun. 22, 2015.
International Search Report issued in connection with International Patent Application No. PCT/US2015/028822 dated Jun. 29, 2015.

* cited by examiner

*Primary Examiner* — William Cheung
(74) *Attorney, Agent, or Firm* — Steven C. Bauman

(57) ABSTRACT

The present invention relates to anaerobic curable compositions, such as adhesives and sealants, containing blocked acrylic acid compounds. The blocked acrylic acid compounds are labile (meth)acrylic acid compounds having an acetal linkage, which cleaves to release (meth)acrylic acid during anaerobic cure. In this way, the block acrylic acid compounds acts as an adhesion promoter thereby promoting adhesion to various substrates.

13 Claims, No Drawings

ANAEROBIC CURABLE COMPOSITIONS CONTAINING BLOCKED (METH)ACRYLIC ACID COMPOUNDS

This application is a Continuation application of application a national stage application filed under 35 USC § 371 of International Application No. PCT/US2015/028908, filed May 1, 2015, which claims the benefit of priority from U.S. Provisional Application No. 62/061,389, filed Oct. 8, 2014, and claims the benefit of priority from U.S. Provisional Application No. 61/987,201, filed May 1, 2014 the entire contents of each of which are incorporated by reference herein as if set forth in their entireties.

BACKGROUND

Field

The present invention relates to anaerobic curable compositions, such as adhesives and sealants, containing blocked (meth)acrylic acid compounds. The blocked (meth)acrylic acid compounds are labile (meth)acrylic acid compounds having an acetal linkage, which cleaves to release (meth)acrylic acid during anaerobic cure. In this way, the block (meth)acrylic acid compounds act as an adhesion promoter thereby promoting adhesion to various substrates.

BRIEF DESCRIPTION OF RELATED TECHNOLOGY

Anaerobic adhesive compositions generally are well-known. See e.g., R. D. Rich, "Anaerobic Adhesives" in Handbook of Adhesive Technology, 29, 467-79, A. Pizzi and K. L. Mittal, eds., Marcel Dekker, Inc., New York (1994), and references cited therein. Their uses are legion and new applications continue to be developed.

Conventional anaerobic adhesives ordinarily include a free-radically polymerizable acrylate ester monomer, together with a peroxy initiator and an inhibitor component. Often, such anaerobic adhesive compositions also contain accelerator components to increase the speed with which the composition cures. Additionally, such compositions may also include adhesion promoters, which can function to increase adhesion to substrates, thereby enhancing adhesive strength.

(Meth)acrylic acid ("AA") is a commonly used adhesion promoter in anaerobic compositions because of its excellent ability to enhance adhesion. However, AA has the disadvantage of being heavily regulated due to its health and safety profile, and thus, requires special considerations during handling, storage, and disposal. These considerations among other things add to cost and inefficiencies. As a result of regulatory scrutiny in certain parts of the world, efforts have been undertaken to identify replacements for AA. To date, these efforts have not provided an acceptable alternative.

It would be advantageous to enjoy the properties conferred upon anaerobic curable compositions AA without the attendant environmental and safety concerns. The present invention provides such a solution.

SUMMARY

In a broad sense, the present invention relates to anaerobic curable compositions, such as adhesives and sealants, containing block (meth)acrylic acid compounds. The blocked (meth)acrylic acid compounds are liable (meth)acrylic acid compounds having an acetal linkage, which cleaves to release (meth)acrylic acid during anaerobic cure. In this way, the blocked (meth)acrylic acid compounds act as an adhesion promoter thereby promoting adhesion to various substrates.

A labile (meth)acrylic acid ("LAA") within the present context is a reaction product that has been prepared from AA and a compound containing a vinyl ether group. The so-formed reaction product provides an acetal compound having a structure represented by AA-B (Compound I) or AA-B-AA (Compound II), where AA represents a (meth)acrylic acid unit, B represents a cleavable blocking unit, joined to AA through an acetal bond. This general structure is referred to herein as a blocked (meth)acrylic acid compound or a labile (meth)acrylic acid compound, or by the acronym, LAA.

The labile (meth)acrylic acid compounds are useful as adhesion promoters for anaerobic curable compositions, such as adhesive and sealant. The labile (meth)acrylic acid compounds provide adhesion promoting properties upon anaerobic cure of the composition. The blocking group is removed under the reaction conditions of anaerobic cure, thereby releasing (meth)acrylic acid to perform its adhesion promoting function. In other words, anaerobic cure conditions cause the cleavage of the acetal bond and re-formation of (meth)acrylic acid and the vinyl ether compound.

The LAA compound may be represented by the structures:

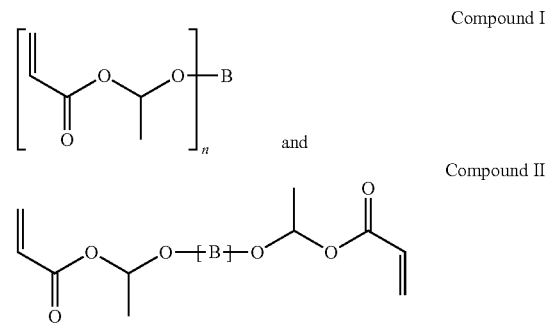

where B is a blocking unit and n=1-2.

In one aspect, there is provided an anaerobic curable composition which includes:

a (meth)acrylate component;

an anaerobic cure system; and a labile (meth)acrylic acid compound.

In another aspect, there is provided an anaerobic curable composition comprising the reaction product of:

a (meth)acrylate component;

an anaerobic cure system; and a labile (meth)acrylic acid compound.

In another aspect, there is provided a method of promoting anaerobic cure of an anaerobic curable composition which includes:

providing a composition which includes:

at least one anaerobically curable component; and an anaerobic cure system; and adding to the composition of step (i) a labile (meth)acrylic acid compound.

DETAILED DESCRIPTION

The following definitions apply here.

The term "(meth)acrylic acid" is intended to include methacrylic acid and acrylic acid.

The term "labile (meth)acrylic acid" or LAA is intended to include compounds which will undergo a chemical change and revert to its starting materials, (meth)acrylic acid and vinyl ether compound, during anaerobic cure. This term is used interchangeably with "blocked (meth)acrylic acid".

The selection of a blocking unit to form the LAA compound is based on several considerations. One such consideration is the ability to "protect" or block the acid group functionality on the AA such that it prevents premature reaction with its surroundings, thereby alleviating health, safety and environmental concerns, all of which require special handling. Thus, the labile compound must be relatively stable under what would be generally considered normal storage, shelf life and manufacturing conditions for reactant ingredients.

This stability must be such that it does not prevent the cleavage of the blocking unit and reformation of AA during anaerobic cure. Thus, during preparation and storage of the LAA, the LAA remains substantially stable, and when incorporated into an anaerobic curable composition, this stability continues until the composition is subjected to anaerobic curing conditions. When subjected to anaerobic curing conditions the AA unit becomes unblocked and AA is released to perform its adhesion promoting function. To achieve these properties, the present invention joins the AA unit to the blocking unit via an acetyl linage. Thus, blocking units which have an available vinyl ether group for reaction with the carboxyl functionality on the AA have been selected.

Another consideration for selection of appropriate blocking units is the compatibility of the blocked (meth)acrylate acid unit [or more accurately, blocked (meth)acrylic acid] with the anaerobic curable composition to which it will be added. Generally, the chosen blocked (meth)acrylate acid has good miscibility and/or solubility with (meth)acrylate monomers or resins and does not react prematurely to any significant extent with any portion of the anaerobic curable composition. Moreover, once the blocking unit and AA units are separated, the blocking unit must not substantially deleteriously affect the anaerobic cure or substantially deleteriously affect the properties of the anaerobic curable composition or the final properties of the cured composition.

Desirably the selected blocking unit is in liquid form for ease of incorporation into the anaerobic curable composition. However, once the AA is unblocked during anaerobic cure, the blocking agent reforms into a vinyl ether compound and is free to participate in the anaerobic polymerization reaction.

Desirable blocking units include vinyl ether compounds. Mono- and di-vinyl ether compounds are contemplated, non-limiting examples of which include those listed in Table I below. The vinyl ether compounds may be used individually or in combination.

TABLE I

| | Compound | CAS | Structure |
|---|---|---|---|
| 1 | Ethyl vinyl ether | 109-92-2 | 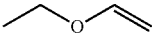 |
| 2 | Isobutyl vinyl ether | 109-53-5 | 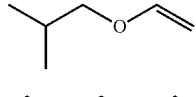 |
| 3 | N-Butyl vinyl ether | 111-34-2 | 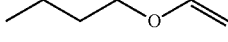 |
| 4 | tert-Butyl vinyl ether | 926-02-3 | 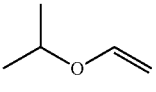 |
| 5 | Cyclohexyl vinyl ether | 2182-55-0 | 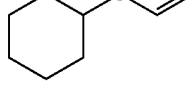 |
| 6 | 1,4-Cyclohexano dimethanol divinyl ether | 17351-75-6 | 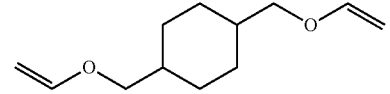 |
| 7 | Butanediol divinyl ether | 3891-33-6 | 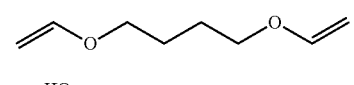 |
| 8 | Hydroxybutyl vinyl ether | 17832-28-9 | 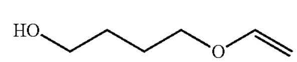 |
| 9 | Diethylene glycol divinyl ether | 764-99-8 | 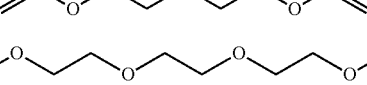 |
| 10 | Triethylene glycol divinyl ether | 765-12-8 | 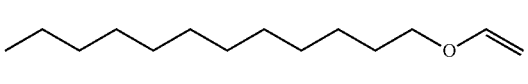 |
| 11 | Dodecyl vinyl ether | 765-14-0 | 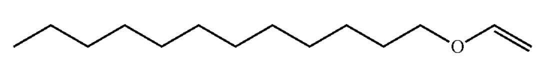 |

TABLE I-continued

| | Compound | CAS | Structure |
|---|---|---|---|
| 12 | Octadecyl vinyl ether | 930-02-9 | CH$_3$(CH$_2$)$_{17}$—O—CH=CH$_2$ |
| 13 | 4-(Hydroxy methyl) cyclohexyl methyl vinyl ether | 114651-37-5 | HOCH$_2$-C$_6$H$_{10}$-CH$_2$-O-CH=CH$_2$ |
| 14 | 2-Ethyl hexyl vinyl ether | 103-44-6 | (2-ethylhexyl)-O-CH=CH$_2$ |
| 15 | Diethylene glycol monovinyl ether | 929-37-3 | HO-CH$_2$CH$_2$-O-CH$_2$CH$_2$-O-CH=CH$_2$ |
| 16 | Poly-THF 290-Divinyl ether | 486438-23-7 | CH$_2$=CH-O-[(CH$_2$)$_4$-O]$_n$-(CH$_2$)$_4$-O-CH=CH$_2$ |
| 17 | 3-Amino propyl vinyl ether | 66415-55-2 | H$_2$N-CH$_2$CH$_2$CH$_2$-O-CH=CH$_2$ |
| 18 | Tert-Amyl vinyl ether | 29281-39-8 | CH$_2$=CH-O-C(CH$_3$)$_2$CH$_2$CH$_3$ |
| 19 | Diethylaminoethyl vinyl ether | 3205-13-8 | (CH$_3$CH$_2$)$_2$N-CH$_2$CH$_2$-O-CH=CH$_2$ |
| 20 | Ethyleneglycol butyl vinyl ether | 4223-11-4 | CH$_3$(CH$_2$)$_3$-O-CH$_2$CH$_2$-O-CH=CH$_2$ |
| 21 | Ethyleneglycol divinyl ether | 764-78-3 | CH$_2$=CH-O-CH$_2$CH$_2$-O-CH=CH$_2$ |
| 22 | Ethyleneglycol monovinyl ether | 764-48-7 | HO-CH$_2$CH$_2$-O-CH=CH$_2$ |
| 23 | Hexanediol divinyl ether | 19763-13-4 | CH$_2$=CH-O-(CH$_2$)$_6$-O-CH=CH$_2$ |
| 24 | Hexanediol monovinyl ether | 27336-16-9 | HO-(CH$_2$)$_6$-O-CH=CH$_2$ |
| 26 | Isopropyl vinyl ether | 926-65-8 | CH$_2$=CH-O-CH(CH$_3$)$_2$ |
| 27 | Polyethyleneglycol-520 methyl vinyl ether | 50856-25-2 | CH$_2$=CHO[CH$_2$CH$_2$O]$_n$CH$_3$ |
| 28 | Pluriol-E200 divinyl ether | 50856-26-3 | CH$_2$=CHO[CH$_2$CH$_2$O]$_n$CH=CH$_2$ |
| 29 | n-Propyl vinyl ether | 764-47-6 | CH$_2$=CH-O-CH$_2$CH$_2$CH$_3$ |
| 30 | Tetraethyleneglycol divinyl ether | 83416-06-2 | CH$_2$=CH-O-(CH$_2$CH$_2$O)$_4$-CH=CH$_2$ |
| 31 | Triethyleneglycol methyl vinyl ether | 26256-87-1 | CH$_3$-O-(CH$_2$CH$_2$O)$_3$-CH=CH$_2$ |
| 32 | Trimethylolpropane trivinyl ether | 57758-90-4 | C(CH$_2$CH$_3$)(CH$_2$-O-CH=CH$_2$)$_3$ |

Preparation of Labile (Meth)Acrylic Acids

The following schematic represents a reaction used to prepare the LAA.

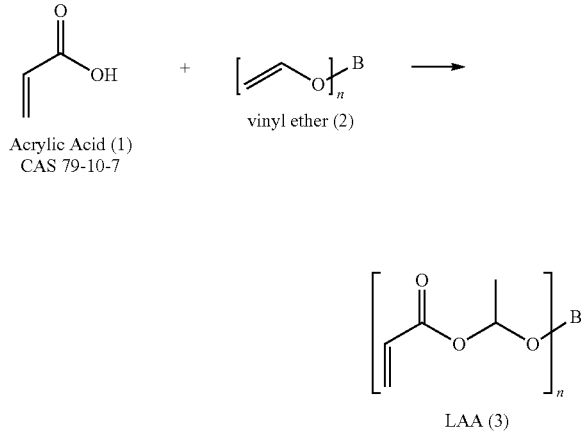

Acrylic Acid (1)
CAS 79-10-7 vinyl ether (2)

LAA (3)

where n=1-2 and B is a hydrocarbon unit, desirably a mono- or di-radical hydrocarbon.

The anaerobic curable composition is based on the (meth)acrylate component, together with an anaerobic cure system, and of course the LAA.

Suitable (meth)acrylate monomers may be chosen from a wide variety of materials, such as those represented by $H_2C=CGCO_2R^1$, where G may be hydrogen, halogen, or alkyl groups having from 1 to about 4 carbon atoms, and $R^1$ may be selected from alkyl, cycloalkyl, alkenyl, cycloalkenyl, alkaryl; aralkyl, or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone, and the like.

Other (meth)acrylate monomers may also be used, such as reaction products of the diglycidylether of bisphenol-A with methacrylic acid and a (meth)acrylate ester corresponding to structure as shown below:

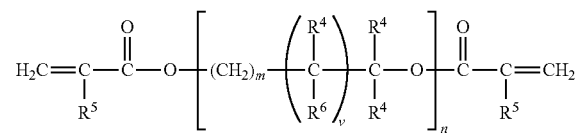

where $R^4$ may be selected from hydrogen, alkyl groups having from 1 to about 4 carbon atoms, hydroxyalkyl groups having from 1 to about 4 carbon atoms or

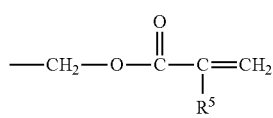

$R^5$ may be selected from hydrogen, halogen, and alkyl groups of from 1 to about 4 carbon atoms;

$R^6$ may be selected from hydrogen, hydroxy and

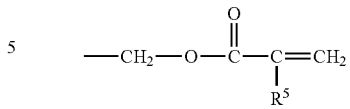

m is an integer equal to at least 1, e.g., from 1 to about 8 or higher, for instance, from 1 to about 4;

v is 0 or 1; and n is an integer equal to at least 1, e.g., 1 to about 20 or more.

Still other (meth)acrylate monomers include silicone (meth)acrylates ("SiMA"), such as those taught by and claimed in U.S. Pat. No. 5,605,999 (Chu), the disclosure of which is hereby expressly incorporated herein by reference.

Additional (meth)acrylate monomers include polyfunctional (meth)acrylate monomers, such as, but not limited to, di- or tri-functional (meth)acrylates like polyethylene glycol di(meth)acrylates, tetrahydrofuran (meth)acrylates and di(meth)acrylates, hydroxypropyl (meth)acrylate ("HPMA"), hexanediol di(meth)acrylate, trimethylol propane tri(meth)acrylate ("TMPTMA"), diethylene glycol dimethacrylate, triethylene glycol dimethacrylate ("TRIEGMA"), tetraethylene glycol dimethacrylate, dipropylene glycol dimethacrylate, di-(pentamethylene glycol) dimethacrylate, tetraethylene diglycol diacrylate, diglycerol tetramethacrylate, tetramethylene dimethacrylate, ethylene dimethacrylate, neopentyl glycol diacrylate, trimethylol propane triacrylate and bisphenol-A mono and di(meth)acrylates, such as ethoxylated bisphenol-A (meth)acrylate ("EBIPMA"), and bisphenol-F mono and di(meth)acrylates, such as ethoxylated bisphenol-F (meth)acrylate.

Combinations of (meth)acrylate monomers may also be used.

The (meth)acrylate component may be present in an amount from about 10 to about 90 percent by weight, such as from about 60 to about 90 percent by weight, based on the total weight of the composition.

Additional components have been included in traditional anaerobic curable compositions to alter the physical properties of either the curable compositions or reaction products thereof, and such additional components may be used in the so-described anaerobic curable compositions.

For instance, one or more of maleimide components, thermal resistance-conferring coreactants, diluent components reactive at elevated temperature conditions, mono- or poly-hydroxyalkanes, polymeric plasticizers, and chelatoxs (see International Patent Application No. PCT/US98/13704, the disclosure of which is hereby expressly incorporated herein by reference) may be included to modify the physical properties and/or cure profile of the formulation and/or the strength or temperature resistance of the cured adhesive.

When used, the maleimide, coreactant, reactive diluent, plasticizer, and/or mono- or poly-hydroxyalkanes, may be present in an amount within the range of about 1 percent to about 30 percent by weight, based on the total weight of the composition.

The anaerobic cure system includes a free-radical initiator, such as a peroxide, and optionally, one or more components selected from free-radical accelerators, free-radical inhibitors, as well as metal catalysts, such as iron and copper.

A number of well-known initiators of free radical polymerization are typically incorporated into anaerobic curable compositions including hydroperoxides, such as cymene hydroperoxides ("CHP"), para-menthane hydroperoxide, t-butyl hydroperoxide ("TBH") and t-butyl perbenzoate. Other initiators of free radical polymerization include peroxides, such as benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, cumene hydroperoxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane and combinations thereof.

Such peroxide compounds are typically employed in the present invention in the range of from about 0.1 to about 10% by weight, based on the total weight of the composition, with about 1 to 5% being desirable.

Accelerators of free radical polymerization may also be used in the compositions of the present invention including, without limitation, organic amides and imides, such as benzoic sulfimide (also known as saccharin) (see U.S. Pat. No. 4,324,349). Such accelerators may also be of the hydrazine variety (e.g., acetyl phenyl hydrazine, APH), as disclosed in U.S. Pat. No. 4,287,350 (Rich) and U.S. Pat. No. 4,321,349 (Rich). Maleic acid is often added to APH-containing anaerobic cure systems. Additional specific accelerators include, without limitation N,N-diethyl-p-toluidine ("DE-p-T") and N,N-dimethyl-o-toluidine ("DM-o-T"). Additional classes of accelerators include thiocaprolactams (e.g., U.S. Pat. No. 5,411,988) and throureas (e.g., U.S. Pat. No. 3,970,505).

When used, accelerators such as saccharin may be present in amounts of about 0.5% to 5% by weight of the total composition.

Stabilizers and inhibitors (such as phenols including hydroquinone and quinones) may also be employed to control and prevent premature peroxide decomposition and polymerization of the composition of the present invention.

Chelating agents, such as the tetrasodium salt of ethylenediamine tetraacetic acid ("EDTA"), may be used to trap trace amounts of metal contaminants. When used, chelating agents may ordinarily be present in the compositions in an amount from about 0.001% by weight to about 0.1% by weight, based on the total weight of the composition.

Metal catalyst solutions or pre-mixes thereof may be used in amounts of about 0.03 to about 0.1% by weight based on the total weight of the composition.

Thickeners, plasticizers, fillers, toughening agents (such as elastomers and rubbers) and other well-known additives may be incorporated herein where the skilled artisan believes it would be desirable to do so.

Also provided are methods of preparing and using the anaerobic curable compositions, as well as reaction products of the compositions.

The anaerobic curable compositions may be prepared using conventional methods that are well known to those persons of skill in the art. For instance, the components may be mixed together in any convenient order consistent with the roles and functions the components are to perform in the compositions. Conventional mixing techniques using known apparatus may be employed.

The anaerobic curable compositions may be applied to a variety of substrates to perform with the desired benefits and advantages described herein. For instance, appropriate substrates may be constructed from steel, brass, copper, aluminum, zinc, and other metals and alloys, ceramics, and thermosets. The compositions of this invention demonstrate particularly good bond strength on surfaces commonly referred to as "active" surfaces, such as iron, brass and copper. An appropriate primer for anaerobic curable compositions may be applied to a surface of the chosen substrate to enhance cure rate.

In addition, a method of preparing an anaerobic curable composition is provided, a step of which includes mixing together a (meth)acrylate component, an anaerobic cure system, and an LAA.

Also provided is a process for bonding using the anaerobic curable composition, the steps of which include applying the composition to a desired substrate surface and exposing the composition to an anaerobic environment for a time sufficient to cure the composition.

Further provided is a method of using an anaerobic cure promoter compound, including (I) mixing the anaerobic cure promoter compound in an anaerobic curable composition or (II) applying onto a surface of a substrate the anaerobic cure promoter compound and applying thereover an anaerobic curable composition. Of course, also provided is a bond formed between mated substrates with the anaerobically curable composition.

In view of the above description, it is clear that a wide range of practical opportunities are provided. The following examples are for illustrative purposes only, and are not to be construed so as to limit in any way the teaching herein.

EXAMPLES

Example 1: Synthesis of Butane Acetal Acrylate (BAA)

Among the more desirable vinyl ether compounds is butyl vinyl ether. An LAA adhesion promoter, butyl acetal acrylate (BAA), was prepared by reacting (meth)acrylic acid with butyl vinyl ether, as described below.

The selection of butyl vinyl ether as the blocking unit provides the following reaction scheme in accordance with the present invention:

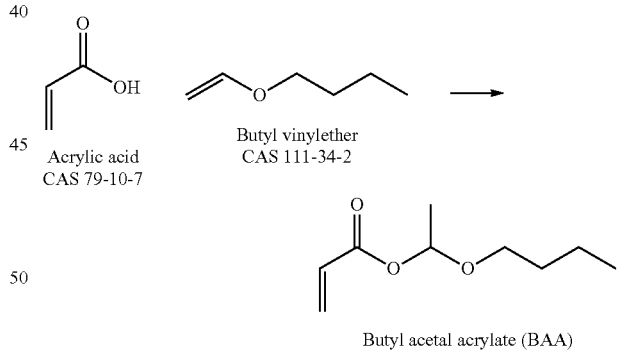

Butyl acetal acrylate (BAA)

Acrylic acid (29.1 g, 400 mmol) and heptane (100 mL) were added to a 500 mL 3-neck round bottom flask (RBF) equipped with magnetic stirring, nitrogen purge, thermo-controlling, pressure-equilibrated addition funnel, and condenser. Butyl vinyl ether (40.88 g, 400 mmol) was added over a few minutes at ambient temperature. Heptane (100 mL) was then added to the RBF. The mixture was warmed to 60° C. Over the next few hours a very mild exotherm was noted.

The reaction was monitored by FT-IR until complete. Once completion was confirmed, the reaction was twice washed with water (100 mL), separated, dried over anhydrous magnesium sulfate, gravity filtered, and concentrated in vacuo at 40° C. and <50 Torr to an oil. The product was then further dried at 40° C. and <1 Torr in a vacuum oven. A clear and colorless oil was obtained, and later identified as butyl acetal acrylate (BAA).

The reaction product structure was verified using FT-IR, $^1$H and $^{13}$C NMR. The following results were obtained:

$^1$H NMR: Solvent DMSOd6, δ 6.30 ppm (d, CH$_2$=), 6.20 ppm (t, —CHC=), 5.90 ppm (m, O—CH—O), 3.55 & 3.45 (t, O—CH$_2$—), 3.35 ppm (solvent exchange, water in DMSOd6), 2.50 ppm (solvent DMSO protons), 1.45 ppm (m, —CH$_2$—), 1.35 ppm (d, —CH$_3$), 1.30 ppm (m, —CH$_2$—), 0.85 ppm (s, CH$_3$—).

$^{13}$C NMR: Solvent DMSOd6, δ 166.0 ppm (C=O), 132.0 (C=CHC—), 128.0 (CH$_2$=C), 97.0 (O—CH—O), 68.0 (O—CH$_2$—C), 40.0 (DMSOd6 solvent), 32.0 (C—CH$_2$—C), 21.0 (C—CH$_3$), 19.0 (C—CH$_2$—C), 15.0 (C—CH$_3$).

FT-IR: ATR Accessory, 2960, 2938 & 2875 (alkyl C—H), 1720 (C=O), 1636 & 1619 (C=C), 1135 (C—O), 836 (—CH$_2$—), 809 (—CH$_3$).

Example 2: Synthesis of 1,4-Butanediol Diacetal Diacrylate (BDDAA)

Among the more desirable vinyl ether compounds is 1,4-butandiol divinyl ether. An LAA adhesion promoter, 1,4-butanediol diacetal diacrylate (BDDAA), was prepared by reacting (meth)acrylic acid with 1,4-butanediol divinyl ether, as described below.

The selection of 1,4-butanediol divinyl ether as the blocking unit provides the following reaction scheme in accordance with the present invention:

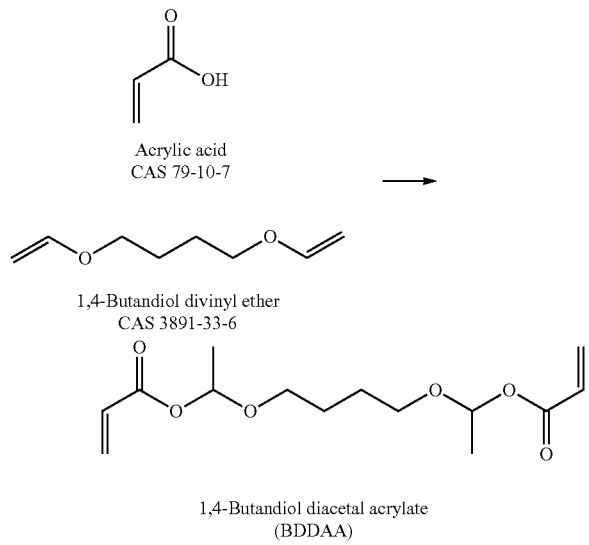

Acrylic acid (29.4 g, 404 mmol) and heptane (100 mL) were added to a 500 mL 3-neck round bottom flask (RBF) equipped with magnetic stirring, nitrogen purge, thermo-controlling, pressure-equilibrated addition funnel, and condenser. Butanediol divinyl ether (29.0 g, 200 mmol) was added over a few minutes at ambient temperature. Heptane (100 mL) was then added to the RBF. Over the next few hours a very mild exotherm was noted.

The reaction was monitored by FT-IR until complete. Once completion was confirmed, the reaction was twice washed with water (100 mL), separated, dried over anhydrous magnesium sulfate, gravity filtered, and concentrated in vacuo at 40° C. and <50 Torr to an oil. The product was then further dried at 40° C. and <1 Torr in a vacuum oven. A clear and colorless oil was obtained, later identified as 1-4-butanediol diacetal diacrylate (BDDAA).

The reaction product structure was verified using FT-IR, $^1$H and $^{13}$C NMR. The following results were obtained:

$^1$H NMR: Solvent DMSOd6, δ 6.30 ppm (d, CH$_2$=), 6.20 ppm (t, —CH=), 5.90 ppm (m, O—CH—O), 3.55 & 3.45 (t, O—CH$_2$—), 335 ppm (solvent exchange, water in DMSOd6), 2.50 ppm (solvent DMSO protons), 1.55 ppm (m, —CH$_2$—), 1.3 ppm (s, CH$_3$—).

$^{13}$C NMR: Solvent DMSOd6, δ 166.0 ppm (C=O), 132.0 (C=CHC—), 128.0 (CH$_2$=C), 97.0 (O—CH—O), 68.0 (O—CH$_2$—C), 40.0 (DMSOd6 solvent), 26.0 (C—CH$_2$—C), 21.0 (C—CH$_3$).

FT-IR: ATR Accessory, 2994, 2942 & 2887 (alkyl C—H), 1717 (C=O), 1636 & 1618 (C=C), 1130 (C—O), 835 (—CH$_2$—), 808 (—CH$_3$).

This compound remained stable during storage in a sealed container at room temperature for 7 months, showing no signs of degradation and remaining unchanged during the storage period.

Further, the compound remained stable when added to an anaerobic curable composition prior to anaerobic cure.

Example 3

The following anaerobic curable compositions were prepared, as shown in Table II. Composition A represents a commercially available retaining compound sold by Henkel Corporation under the product name Retaining Compound 638. This composition uses free, (unblocked) (meth)acrylic acid as an adhesion promoter. Composition B is an inventive composition and has a substantially identical composition to composition A except the LAA of the present invention is used in place of the free AA. Finally, composition C has substantially the identical composition as A and B, except neither free AA nor LAA is present.

TABLE II

| | Composition/(wt %) | | |
|---|---|---|---|
| Component | A | B | C |
| Hydroxypropylmethacrylate | 14.5 | 13.5 | 15.5 |
| (Meth)acrylate Resin | 74.45 | 69.45 | 79.51 |
| Acrylic Acid | 6.06 | — | — |
| LAA (Blocked Acrylic Acid)[1] | — | 12.06 | — |
| Napthaquinone[2] | 0.19 | 0.19 | 0.19 |
| EDTA[3] | 0.96 | 0.96 | 0.96 |
| Saccharin | 0.96 | 0.96 | 0.96 |
| APH[4] | 0.96 | 0.96 | 0.96 |
| CHP[5] | 1.92 | 1.92 | 1.92 |
| Total | 100 | 100 | 100 |

[1] 1,4-butanediol diacetal acrylate; added on a percent weight basis that is equimolar to the amount of acrylic acid used in Example A;
[2] 5% NQ in polyethyleneglycol (meth)acrylate mixture;
[3] 3.5% solution;
[4] 1-acetyl-2-phenylhydrazine;
[5] cumene hydroperoxide.

As noted from Table II, Compositions A and C are comparative examples, with Composition A using conventional acrylic acid as an adhesion promoter, and Composition C not using any acrylic acid adhesion promoter. Composition B is a labile (meth)acrylic acid compound.

Each of the anaerobic curable compositions A-C was used to bond degreased steel pins and collars together. Anaerobic cure took place at room temperature. The results of compressive shear strength tests (5 replications) on pin and collar assemblies are shown in Table III. Standard pins (12.6 mm diameter) and collars (12.7 mm wide diameter) were used with a diametral clearance of about 0.25-0.075 mm.

TABLE III

Comparative Shear Strength (psi)

| Composition | Time (hours) | | |
|---|---|---|---|
| | 1 | 4 | 24 |
| A | 2000 ± 105 | 2859 ± 275 | 2949 ± 364 |
| B | 3181 ± 341 | 3007 ± 320 | 3015 ± 233 |
| C | 2617 ± 248 | 2523 ± 138 | 2561 ± 406 |

Comparative shear strengths were conducted using ASTM D4562, ISO 10123, and MIL-R-46082 standard test methods. A tension/comparison testing machine equipped with a suitable cell load and capable of maintaining a constant displacement rate was used. The pin/collar test specimens were placed on a texture which supported the collar but not the pin and allowed for the pin to be placed under compressive force and to move relative to the collar when the adhesive bond failed. The crosshead speed of the testing machine was 2 mm/min.

Compressive shear strengths were calculated as:

$$S = L/A$$

where S=N/mm² (shear strength psi); L=N (load at failure lbs.); and A=bond area in mm² (in.²).

Compressive shear strengths as shown in Table III demonstrate substantially better strengths for the Composition B as compared to Compositions A and C.

The thermal stability for Composition B is within the acceptable range for an anaerobic retaining compound. Moreover, with storage at ambient temperature the stability of the 3 compositions was unchanged over 4 months. The ambient stability of the 3 compositions is summarized in Table IV, below.

TABLE IV

Ambient Stability

| Composition | Initial | | | 4 Months | | |
|---|---|---|---|---|---|---|
| | Solubility | Stability | Visual Inspection | Solubility | Stability | Visual Inspection |
| A | OK | OK | OK | OK | OK | Unchanged |
| B | OK | OK | OK | OK | OK | Unchanged |
| C | OK | OK | OK | OK | OK | Unchanged |

Example 4

The following anaerobic curable compositions were prepared as shown in Table V. Composition D represents a control retaining compound using free (meth)acrylic acid (unblocked) as an adhesion promoter. Composition E has a substantially identical composition to Composition A, except LAA is used in place of the free AA.

TABLE V

| | Composition/(wt %) | |
|---|---|---|
| Component | D | E |
| Hydroxypropylmethacrylate | 14.5 | 12.9 |
| (Meth)acrylate Resin | 74.45 | 67.62 |
| Acrylic Acid | 6.06 | — |
| LAA (Blocked Acrylic Acid)[1] | — | 14.49 |
| Napthaquinone[2] (NQ) | 0.19 | 0.19 |
| EDTA[3] | 0.96 | 0.96 |
| Saccharin | 0.96 | 0.96 |
| APH[4] | 0.96 | 0.96 |
| CHP[5] | 1.92 | 1.92 |
| | 100 | 100 |

[1] butyl acetal acrylate (BAA); added on a percent weight basis that is equimolar to the amount of acrylic acid used in Example A;
[2] 5% NQ in polyethyleneglycol (meth)acrylate mixture;
[3] 3.5% solution;
[4] 1-acetyl-2-phenylhydrazine;
[5] cumene hydroperoxide.

Both of the anaerobic curable compositions were used to bond degreased steel pins and collars together. Anaerobic cure took place at room temperature. The results of compressive shear strength tests (5 replications) on pin and collar assemblies are shown in Table VI. Standard pins (12.6 mm diameter) and collars (12.7 mm wide diameter) were used with a diametral clearance of about 0.25-0.075 mm.

TABLE VI

Comparative Shear Strength (psi)

| Composition | Time (Hours) | | |
|---|---|---|---|
| | 1 | 4 | 24 |
| D | 3447 ± 629 | 3295 ± 486 | 2737 ± 506 |
| E | 2765 ± 371 | 3535 ± 597 | 2932 ± 314 |

Comparative shear strengths were conducted using ASTM D4562, ISO 10123, and MIL-R-46082 standard test methods. A tension/comparison testing machine equipped with a suitable cell load and capable of maintaining a constant displacement rate was used. The pin/collar test specimens were placed on a texture which supported the collar but not the pin and allowed for the pin to be placed under compressive force and to move relative to the collar when the adhesive bond failed. The crosshead speed of the testing machine was 2 mm/min.

Compressive shear strengths were calculated as shown in Example 3.

Compressive shear strengths as shown in Table VI demonstrate better strengths for the Composition E as compared to Composition D at 4 and 24 hours.

The thermal stability for Composition E is within the acceptable range for an anaerobic retaining compound. Moreover, with storage at ambient temperature the stability of the 2 compositions was unchanged over 13 days. The ambient stability of the two compositions is summarized in Table VII, below.

TABLE VII

| | Ambient Stability | | | | | |
|---|---|---|---|---|---|---|
| | Initial | | | 13 days | | |
| Composition | Solubility | Stability | Visual Inspection | Solubility | Stability | Visual Inspection |
| D | OK | OK | OK | OK | OK | Unchanged |
| E | OK | OK | OK | OK | OK | Unchanged |

The invention claimed is:

1. An anaerobic curable composition comprising:
 (i) a (meth)acrylate component;
 (ii) an anaerobic cure system; and
 (iii) an adhesion promoter comprising a labile (meth)acrylic acid compound, wherein the labile (meth)acrylic acid compound is the reaction product of (meth)acrylic acid and a vinyl ether compound selected from the group consisting of ethyl vinyl ether; isobutyl vinyl ether; n-butyl vinyl ether; tert-Butyl vinyl ether; cyclohexyl vinyl ether; 1,4-cyclohexane dimethanol divinyl ether; butanediol divinyl ether; hydroxybutyl vinyl ether; diethylene glycol divinyl ether; triethylene glycol divinyl ether; dodecyl vinyl ether; octadecyl vinyl ether; 4-(hydroxy methyl) cyclohexyl methyl vinyl ether; 2-ethyl hexyl vinyl ether; diethylene glycol monovinyl ether; poly-THF 290-divinyl ether; 3-amino propyl vinyl ether; tertamyl vinyl ether; diethylaminoethyl vinyl ether; ethyleneglycol butyl vinyl ether; ethyleneglycol divinyl ether; ethyleneglycol monovinyl ether; hexanediol divinyl ether; hexanediol monovinyl ether; isopropyl vinyl ether; polyethyleneglycol-520 methyl vinyl ether; pluriol-E200 divinyl ether; n-propyl vinyl ether; tetraethyleneglycol divinyl ether; triethyleneglycol methyl vinyl ether; and trimethylolpropane trivinyl ether.

2. The composition of claim 1 wherein the labile (meth)acrylic acid compound is an acetal compound.

3. An anaerobic curable composition comprising:
 (i) a (meth)acrylate component;
 (ii) an anaerobic cure system; and
 (iii) an adhesion promoter comprising a labile (meth)acrylic acid compound, wherein the labile (meth)acrylic acid compound is the reaction product of a vinyl ether compound and (meth)acrylic acid.

4. An anaerobic curable composition comprising:
 (i) a (meth)acrylate component;
 (ii) an anaerobic cure system; and
 (iii) an adhesion promoter comprising a labile (meth)acrylic acid compound, wherein the labile (meth)acrylic acid compound is embraced by:

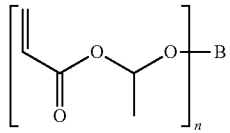

wherein B is a blocking unit and n is 1-2.

5. The composition of claim 1 wherein the (meth)acrylate component is represented by:
 $H_2C=CGCO_2R^1$, wherein G may be hydrogen, halogen, or alkyl groups having from 1 to about 4 carbon atoms, and R1 may be selected from alkyl, cycloalkyl, alkenyl, cycloalkenyl, alkaryl, aralkyl, or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate and sulfone;
 reaction products of the diglycidylether of bisphenol-A with methacrylic acid and a (meth)acrylate ester corresponding to structure as shown below:

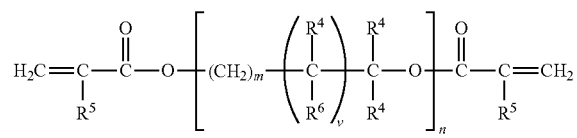

where $R^4$ may be selected from hydrogen, alkyl groups having from 1 to about 4 carbon atoms, hydroxyalkyl groups having from 1 to about 4 carbon atoms or

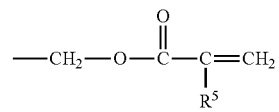

$R^5$ may be selected from hydrogen, halogen, and alkyl groups of from 1 to about 4 carbon atoms;
$R^6$ may be selected from hydrogen, hydroxy and

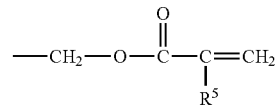

m is an integer equal to at least 1, e.g., from 1 to about 8 or higher, for instance, from 1 to about 4;
v is 0 or 1; and
n is an integer equal to at least 1, e.g., 1 to about 20 or more; and
polyfunctional (meth)acrylate monomers, di- or trifunctional (meth) acrylates, polyethylene glycol di(meth)acrylates, tetrahydrofuran (meth)acrylates and di(meth)acrylates, hydroxypropyl (meth)acrylate, hexanediol di(meth)acrylate, trimethylol propane tri(meth)acrylate, diethylene glycol dimethacrylate, triethylene glycol dimethacrylate, tetraethylene glycol dimethacrylate, dipropylene glycol dimethacrylate, di-(pentamethylene glycol) dimethacrylate, tetraethylene diglycol diacrylate, diglycerol tetramethacrylate, tetramethylene dimethacrylate, ethylene dimethacrylate, neopentyl glycol diacrylate, trimethylol propane triacrylate, bisphenol-A mono and di(meth)acrylates, ethoxylated bisphenol-A (meth)acrylate, and bisphenol-F mono and di(meth)acrylates, and ethoxylated bisphenol-F (meth)acrylate.

6. The composition of claim 1 wherein the anaerobic cure system comprises a free-radical initiator.

7. A composition comprising the reaction product of:
 (i) a (meth)acrylate component;
 (ii) an anaerobic cure system; and
 (iii) an adhesion promoter comprising a labile (meth)acrylic acid compound, wherein the labile (meth)acrylic acid compound is the reaction product of (meth)acrylic acid and a vinyl ether compound selected from the group consisting of ethyl vinyl ether; isobutyl vinyl ether; n-butyl vinyl ether; tert-Butyl vinyl ether; cyclohexyl vinyl ether; 1,4-cyclohexane dimethanol divinyl ether; butanediol divinyl ether; hydroxybutyl vinyl ether; diethylene glycol divinyl ether; triethylene glycol divinyl ether; dodecyl vinyl ether; octadecyl vinyl ether; 4-(hydroxy methyl) cyclohexyl methyl vinyl ether; 2-ethyl hexyl vinyl ether; diethylene glycol monovinyl ether; poly-THF 290-divinyl ether; 3-amino propyl vinyl ether; tertamyl vinyl ether; diethylaminoethyl vinyl ether; ethyleneglycol butyl vinyl ether; ethyleneglycol divinyl ether; ethyleneglycol monovinyl ether; hexanediol divinyl ether; hexanediol monovinyl ether; isopropyl vinyl ether; polyethyleneglycol-520 methyl vinyl ether; pluriol-E200 divinyl ether; n-propyl vinyl ether; tetraethyleneglycol divinyl ether; triethyleneglycol methyl vinyl ether; and trimethylolpropane trivinyl ether.

8. A method of making an anaerobic curable composition comprising:
   (i) Providing a composition comprising:
      (a) a (meth)acrylate component; and
      (b) an anaerobic cure system; and
   (ii) Adding to the composition of step (i) an adhesion promoter comprising a labile (meth)acrylic acid compound, wherein the labile (meth)acrylic acid compound is the reaction product of (meth)acrylic acid and a vinyl ether compound selected from the group consisting of ethyl vinyl ether; isobutyl vinyl ether; n-butyl vinyl ether; tert-Butyl vinyl ether; cyclohexyl vinyl ether; 1,4-cyclohexane dimethanol divinyl ether; butanediol divinyl ether; hydroxybutyl vinyl ether; diethylene glycol divinyl ether; triethylene glycol divinyl ether; dodecyl vinyl ether; octadecyl vinyl ether; 4-(hydroxy methyl) cyclohexyl methyl vinyl ether; 2-ethyl hexyl vinyl ether; diethylene glycol monovinyl ether; poly-THF 290-divinyl ether; 3-amino propyl vinyl ether; tertamyl vinyl ether; diethylaminoethyl vinyl ether; ethyleneglycol butyl vinyl ether; ethyleneglycol divinyl ether; ethyleneglycol monovinyl ether; hexanediol divinyl ether; hexanediol monovinyl ether; isopropyl vinyl ether; polyethyleneglycol-520 methyl vinyl ether; pluriol-E200 divinyl ether; n-propyl vinyl ether; tetraethyleneglycol divinyl ether; triethyleneglycol methyl vinyl ether; and trimethylolpropane trivinyl ether.

9. A composition comprising the reaction product of:
   (i) a (meth)acrylate component;
   (ii) an anaerobic cure system; and
   (iii) an adhesion promoter comprising a labile (meth) acrylic acid compound, wherein the labile (meth) acrylic acid compound is the reaction product of a vinyl ether compound and (meth)acrylic acid.

10. A composition comprising the reaction product of:
   (i) a (meth)acrylate component;
   (ii) an anaerobic cure system; and
   (iii) an adhesion promoter comprising a labile (meth) acrylic acid compound, wherein the labile (meth) acrylic acid compound is embraced by:

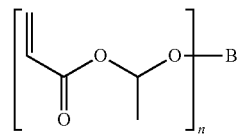

wherein B is a blocking unit and n is 1-2.

11. A method of making an anaerobic curable composition comprising:
   (i) Providing a composition comprising:
      (a) a (meth)acrylate component; and
      (b) an anaerobic cure system; and
   (ii) Adding to the composition of step (i) an adhesion promoter comprising a labile (meth)acrylic acid compound, wherein the labile (meth)acrylic acid compound is the reaction product of a vinyl ether compound and (meth)acrylic acid.

12. A method of making an anaerobic curable composition comprising:
   (i) Providing a composition comprising:
      (a) a (meth)acrylate component; and
      (b) an anaerobic cure system; and
   (ii) Adding to the composition of step (i) an adhesion promoter comprising a labile (meth)acrylic acid compound, wherein the labile (meth)acrylic acid compound is embraced by:

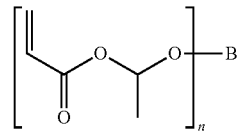

wherein B is a blocking unit and n is 1-2.

13. The composition of claim 6, wherein the anaerobic cure system further comprises one or more free-radical accelerators.

* * * * *

UNITED STATES PATENT AND TRADEMARK OFFICE
CERTIFICATE OF CORRECTION

PATENT NO. : 9,994,510 B2
APPLICATION NO. : 15/340385
DATED : June 12, 2018
INVENTOR(S) : Andrew D. Messana et al.

It is certified that error appears in the above-identified patent and that said Letters Patent is hereby corrected as shown below:

In the Specification

Column 4, Table 1, No. 6: change "1,4-Cyclohexano dimethanol divinyl ether" to -- 1,4-Cyclohexane dimethanol divinyl ether --
Column 8, Line 48: change "chelatoxs" to -- chelators --
Column 11, Line 8: change "(t, -CHC=)" to -- (t, -CH=) --
Column 12, Line 45: change "Hydroxypropyhmethacrylate" to -- Hydroxypropylmethacrylate --

Signed and Sealed this
Eighteenth Day of June, 2019

Andrei Iancu
*Director of the United States Patent and Trademark Office*